United States Patent [19]

Mueller et al.

[11] Patent Number: 4,994,603

[45] Date of Patent: Feb. 19, 1991

[54] PREPARATION OF METHYL FORMATE

[75] Inventors: Franz-Josef Mueller, Wachenheim; Wolfgang Steiner, Friedelsheim; Karl-Heinz Ross, Mutterstadt; Otto Kratzer, Bobenheim-Roxheim, all of Fed. Rep. of Germany

[73] Assignee: BASF Aktiengesellschaft, Ludwigshaften, Fed. Rep. of Germany

[21] Appl. No.: 299,544

[22] Filed: Sep. 4, 1981

[30] Foreign Application Priority Data

Oct. 1, 1980 [DE]  Fed. Rep. of Germany ....... 3037089

[51] Int. Cl.$^5$ ...................... C07C 67/36; C07C 69/06
[52] U.S. Cl. .............................................. 560/232
[58] Field of Search ........................................ 560/232

[56] References Cited

FOREIGN PATENT DOCUMENTS

| 3221239 | 12/1983 | Fed. Rep. of Germany ...... 560/232 |
| 207460 | 2/1984 | German Democratic Rep. ................................... 560/232 |
| 1047408 | 11/1966 | United Kingdom ................ 560/232 |

OTHER PUBLICATIONS

Moiseev, I. I., et al., (U.S.S.R.), Visn. L'viv Politekh Inst., 1980, 139, 146-9, (Russ.).

*Primary Examiner*—Vivian Garner
*Attorney, Agent, or Firm*—John H. Shurtleff

[57] ABSTRACT

A process for the preparation of methyl formate by reacting methanol and carbon monoxide in the presence of an alkali metal alcoholate or alkaline earth metal alcoholate at from 30° to 150° C. and from 50 to 300 bar, wherein a nonionic complexing agent is used to bind the alkali metal cations or alkaline earth metal cations.

8 Claims, No Drawings

PREPARATION OF METHYL FORMATE

The present invention relates to an improved process for the preparation of methyl formate by reacting methanol and carbon monoxide in the presence of an alkali metal alcoholate or alkaline earth metal alcoholate at 30°–150° C. and 50–300 bar.

This process, apart from the improvement according to the invention, is well-known, cf. Ullmann, "Enzyklopädie der Technischen Chemie", 3rd edition (1953), Volume 3, pages 450–451.

However, carrying out this synthesis industrially presents technical difficulties due to the fact that the solubility of the alcoholates in the reaction mixture decreases with increasing conversion of methanol, so that salt deposits and crusts are formed in the apparatus. This not only interferes with the synthesis of the methyl formate but also with working up of the reaction mixture by distillation.

It is an object of the present invention to remedy the above disadvantages by substantially suppressing the deposition of salt.

We have found that this object is achieved by a process for the preparation of methyl formate by reacting methanol and carbon monoxide in the presence of an alkali metal alcoholate or alkaline earth metal alcoholate at from 30° to 150° C. and from 50 to 300 bar, wherein a non-ionic complexing agent is used to bind the alkali metal cations or alkaline earth metal cations.

Suitable complexing agents are, in particular, cyclic and acyclic compounds, in which the characteristic feature of their complexing capability is the polyethylene glycol structural unit $$-(-O-CH_2-CH_2-)_n-O-\ n=2-12.$$

In these compounds, the oxygen atoms of the structural units can also be replaced by S or, in particular, by —NH—.

Examples of commercial compounds of this type are 1,4,7,10,13-pentaoxa[13]orthocyclophane (Benzo-15-C-5), 1,4,7,14,17,20-hexaoxa-[7,7]orthocyclophane (Dibenzo-18-C-6), 1,4,7,10,17,20,23,26-octaoxa[10,1-0]orthocyclophane (Dibenzo-24-C-8), 2,5,8,15,18,21-hexaoxatricyclo[20,4,0,0$^{9,14}$]hexacosane (Dicyclohexyl-18-C-6), 1,4,7,10-tetraoxacyclododecane (12-C-4), 1,4,7,10,13-pentaoxacyclopentadecane (15-C-5), 1,4,7,10,13,16-hexaoxacyclooctadecane (18-C-6), 4,7,13,18-tetraoxa-1,10-diazabicyclo[8,5,5]eicoxane and 4,7,13,16,21-pentaoxa-1,10-diazabicyclo[8,8,6]tricosane.

Other suitable compounds are, inter alia, polyethylene glycol dialkyl ethers (where alkyl is, for example, of 1 to 4 carbon atoms), triethanolamine and tetraalkylethylenediamines (where alkyl is, for example, of 1 to 4 carbon atoms).

Further details of these and other suitable complexing agents are to be found in the review by Vögtle and Weber, Angew. Chem., 91 (1979), 813 et seq. The acyclic and cyclic crown ethers are described in this article which is also available in the English language edition, Angew. Chem. Int. Ed. Engl. 18, 753–776 (1979).

Advantageously, the complexing agents are employed in at least the stoichiometric amount relative to the alkali metal cations or alkaline earth metal cations. In most cases, the best results are achieved by employing from 1.0 to 10.0 moles of the complexing agent per gram equivalent of the cation.

The complexing agents keep the alkali metal alcoholates and alkaline earth metal alcoholates substantially in solution, so that far smaller amounts of salt-like deposits form.

The complexing agents further offer a particular advantage in respect of working up the reaction mixture by distillation. In their presence, the methyl formate can be distilled completely from the methanolic catalyst solution, without deposits and crusts forming in the distillation apparatus.

In other respects, the methyl formate synthesis is carried out in a conventional manner, i.e. at 30°–150° C., preferably 60°–120° C., and under a carbon monoxide pressure of 50–300 bar, preferably 200–250 bar.

Suitable catalysts, in addition to the alcoholates of the alkaline earth metals, for example calcium, strontium or barium, are, in particular, the alcoholates of the alkali metals lithium, sodium and potassium; as a rule the use of sodium alcoholate is the most economical and is therefore particularly advisable. In principle, the alcoholate used can be derived from any alcohol, but generally there is no reason to use a different alcoholate from that derived from methanol, since the latter is in any case present in the system.

The amount of catalyst used is as a rule from 0.001 to 0.1, preferably from 0.001 to 0.01, mole per mole of methanol.

EXAMPLES 1–9 and COMPARATIVE EXAMPLES 1C–3C 100 ml (2.5 moles) of methanol were converted to methyl formate at 90° C. under a carbon monoxide pressure of p bar in the course of t hours in the presence of a moles of an alkali metal methylate and b moles of a complexing agent. The results of these experiments, in respect of yield of methyl formate, color of the reaction mixture and amount of salt-like precipitate formed, are shown in the Table.

TABLE

Results of Examples 1–9 and Comparative Examples 1C–3C

| Example | Pressure p [bar] | Time t [h] | Alkali metal | a [moles] | Complexing agent Type | b [moles] | Color of reaction mixture | Yield of methyl formate [%] | Precipitate [g] |
|---|---|---|---|---|---|---|---|---|---|
| 1C | 250 | 3 | Na | 0.006 | — | — | yellow | 98.0 | 1.13 |
| 1 | " | " | " | " | Polyethylene glycol mixture HO—(—CH$_2$—CH$_2$—O—)$_n$—H, n = 3 – 10 | 0.005 | yellow | 98.0 | 0.5 |
| 2 | " | " | " | " | Polyethylene glycol mixture HO—(—CH$_2$—CH$_2$—O—)$_n$—H, n = 3 – 10 | 0.01 | yellow | 98.0 | 0.1 |
| 3 | " | " | " | " | Crown ether 1,4,7,10,13-pentaoxacyclopentadecane (15-Crown-5) | 0.01 | colorless | 96.0 | 0.15 |

TABLE-continued
Results of Examples 1- and Comparative Examples 1C–3C

| Example | Pressure p [bar] | Time t [h] | Alkali metal | a [moles] | Complexing agent Type | b [moles] | Color of reaction mixture | Yield of methyl formate [%] | Precipitate [g] |
|---|---|---|---|---|---|---|---|---|---|
| 4 | " | " | " | " | Diethylene glycol dimethyl ether | 0.015 | brownish | 94.2 | 0.44 |
| 2C | 200 | 8 | Li | 0.003 | — | — | yellow | 92.5 | 0.56 |
| 5 | " | " | " | " | 4,7,13,18-Tetraoxa-1,10-diazabicyclo[8,5,5]eicosane | 0.002 | brownish | 93.0 | 0.24 |
| 6 | " | " | " | " | Tetramethylethylenediamine | 0.015 | yellow | 93.3 | 0.10 |
| 7 | " | " | " | " | Triethanolamine | 0.005 | yellow | 93.6 | 0.11 |
| 3C | 230 | " | Na | 0.006 | — | — | yellow | 94.6 | 0.44 |
| 8 | " | " | " | " | 4,7,13,16,21-Pentaoxa-1,10-diazabicyclo[8,8,5]tricosane | 0.002 | colorless | 99.0 | 0.10 |
| 9 | " | " | " | " | 1,4,7,10,13-Pentaoxacyclopentadecane | 0.002 | brownish | 91.6 | 0.11 |

We claim:

1. A process for the preparation of methyl formate which comprises reacting methanol and carbon monoxide in the presence of sodium methylate at a temperature of 30° to 150° C. and a pressure of 5 to 300 bar, binding the sodium cation of said sodium methylate with a nonionic complexing agent selected from the group consisting of acyclic compounds containing a polyethylene glycol structural unit $$-(-OCH_2-CH_2-)_n-O-$$

where n=2 to 12.

2. A process as claimed in claim 1 wherein the methyl formate is substantially completely distilled from the reaction mixture containing the complexed sodium.

3. A process as claimed in claim 1 wherein the sodium methylate is present in a catalytic amount of about 0.001 to 0.1 mole per mole of methanol.

4. A process as claimed in claim 3 wherein the complexing agent is used in at least a stoichiometric amount with reference to the sodium cation of said sodium methylate.

5. A process for the preparation of methyl formate which comprises reacting methanol and carbon monoxide in the presence of sodium methylate at a temperature of 30° to 150° C. and a pressure of 5 to 300 bar, binding the sodium cation of said sodium methylate with a nonionic complexing agent which is a cyclic crown ether containing a polyethylene glycol structural unit $$-(-OCH_2-CH_2-)_n-O-$$

where n=3 to 12.

6. A process as claimed in claim 5 wherein the methyl formate is substantially completely distilled from the reaction mixture containing the complexed sodium.

7. A process as claimed in claim 5 wherein the sodium methylate is present in a catalytic amount of about 0.001 to 0.1 mole per mole of methanol.

8. A process as claimed in claim 5 wherein the complexing agent is used in at lest a stoichiometric amount with reference to the sodium cation of said sodium methylate.

* * * * *

UNITED STATES PATENT AND TRADEMARK OFFICE
CERTIFICATE OF CORRECTION

PATENT NO. : 4,994,603

DATED : Feb. 19, 1991

INVENTOR(S) : Franz-Josef Mueller, Wolfgang Steiner, Karl-Heinz Ross and Otto Kratzer It is certified that error appears in the above-identified patent and that said Letters Patent is hereby corrected as shown below:

COL. 3  Claim 1, line 28, change the structural formula
" $-(-OCH_2-CH_2-)hd\ n\ -O-$ " to read -- $-(-OCH_2-CH_2-)_n-O-$ --.

Signed and Sealed this

Twenty-fourth Day of November, 1992

Attest:

DOUGLAS B. COMER

Attesting Officer    Acting Commissioner of Patents and Trademarks